US005099082A

United States Patent [19]

Bolmer et al.

[11] Patent Number: 5,099,082

[45] **Date of Patent: * Mar. 24, 1992**

[54] SOLVENT EXTRACTION OF I-141B FROM I-365

[75] Inventors: Michael S. Bolmer, Lower Providence; Maher Y. Elsheikh, Tredyffrin, both of Pa.

[73] Assignee: Atochem North America, Inc., Philadelphia, Pa.

[ * ] Notice: The portion of the term of this patent subsequent to Mar. 24, 2009 has been disclaimed.

[21] Appl. No.: 751,023

[22] Filed: Aug. 28, 1991

[51] Int. Cl.[5] .......... C07C 17/38

[52] U.S. Cl. .......... 570/180

[58] Field of Search .......... 570/180

[56] References Cited

U.S. PATENT DOCUMENTS 3,624,166 11/1971 Fuhrmann et al. .......... 570/180

3,947,558 3/1976 Eijl .......... 570/180

4,031,148 6/1977 Helgorsky .

*Primary Examiner*—Alan Siegel

[57] ABSTRACT

Partial or total separation of a mixture of 1,1,1,3,3-pentafluorobutane and 1,1-dichloro-1-fluoroethane by liquid-liquid extraction with solvents containing ethylene glycol, 2-butene-1,4-diol, ethanolamine, propylene glycol, or mixtures thereof, preferably ethylene glycol.

3 Claims, 2 Drawing Sheets

SOLVENT EXTRACTION OF I-141B FROM I-365

FIELD OF THE INVENTION

This invention relates to a method of partially or totally separating a mixture of 1,1,1,3,3-pentafluorobutane ("I-365") and 1,1-dichloro-1-fluoroethane ("I-141b") by liquid-liquid extraction with solvents containing ethylene glycol, 2-butene-1,4-diol, ethanolamine, propylene glycol, or mixtures thereof.

BACKGROUND OF THE INVENTION

I-365 is a byproduct formed during the manufacture of I-141b, a replacement for trichlorofluoromethane as a blowing agent. Since I-365 is a solvent and precursor for other chemicals, a method for its recovery is needed. Separation by conventional distillation means is extremely difficult, however, since I-365 and I-141b form an azeotrope.

While liquid-liquid extraction has been reported in U.S. Pat. No. 4,031,148 for separating chlorinated hydrocarbons by the use of water-miscible solvents and 0%-50% water, applicant is not aware of literature which discloses liquid-liquid extraction for separating HFC's (hydrofluorocarbons) such as I-365 from HCFC's (hydrochlorofluorocarbons) such as I-141b. Also, as noted in column 1, lines 53-56 of said U.S. Pat. No. 4,031,148, and as demonstrated by copending application Ser. No. 07/751,014, filed on even date herewith, it is impossible to foresee which extraction agents will enable the separation of any two substances.

SUMMARY OF THE INVENTION

A method is provided for at least partial separation of a mixture of I-365 and I-141b comprising liquid-liquid extraction on the mixture in the presence of a solvent containing ethylene glycol, 2-butene-1,4-diol, ethanolamine, propylene glycol, or mixtures thereof, preferably ethylene glycol. More specifically, the process comprises contacting the mixture of I-141b and I-365 with the extracting agent such that the agent extracts I-141b from the mixture and forms a separate phase therefrom, then separating the phases of I-141b-rich solvent and I-141b/I-365 mixture, which mixture now has a correspondingly reduced concentration of I-141b.

DETAILED DESCRIPTION OF THE INVENTION

It has now been discovered that efficient separation of I-365 and I-141b can be achieved via liquid-liquid extraction using the aforementioned solvents, such as ethylene glycol alone or in admixture with 2-butene-1,4-diol, ethanolamine, propylene glycol, propylene carbonate, or 2-butene-1,4-diol and propylene glycol; 2-butene-1,4-diol alone or in admixture with propylene glycol, ethanolamine, or propylene carbonate; ethanolamine alone or with propylene glycol; or propylene glycol. These solvents are found to have a selectivity for I-141b (at 25° C.) of from about 1.24 to 3.85. Other solvents, such as dipropylene glycol, may be incorporated as well as long as the selectivity is not substantially adversely affected. Subject to this proviso, the exact proportion of solvent components in the solvent mixtures is not critical. Examples of solvent mixtures containing dipropylene glycol ("DG") are DG in admixture with ethanolamine, 2-butene-1,4-diol, 2-butene-1,4-diol and ethanolamine, ethylene glycol and ethanolamine, or ethylene glycol and 2-butene-1,4-diol.

Figure 1:
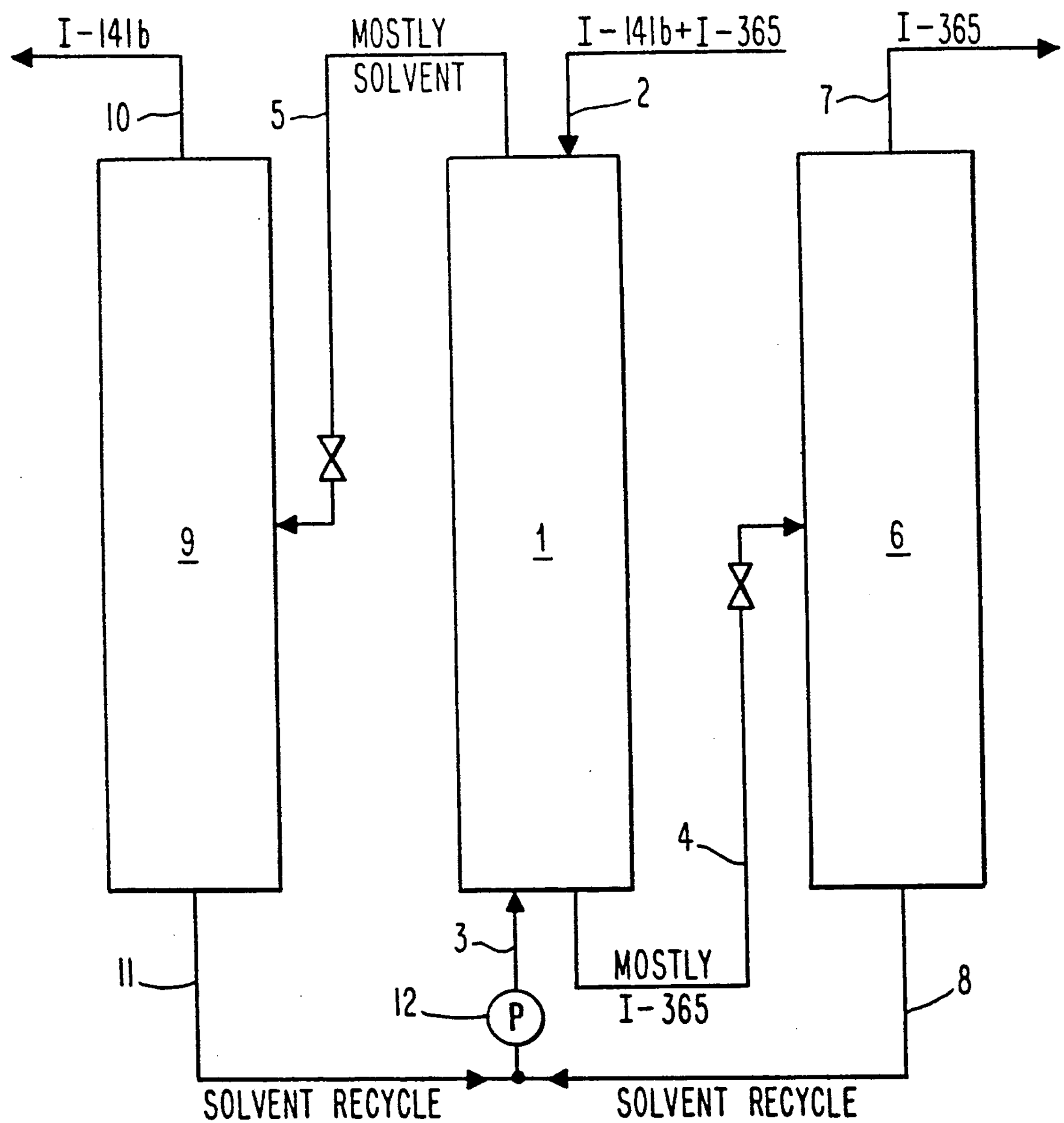
FIG. 1 is a schematic illustration of a liquid-liquid extraction system.

The separation can be carried out in a liquid-liquid extractor, as shown in FIG. 1, where a I-141b/I-365 mixture is shown as the heavier component entering the top of the extraction column 1 through line 2. The solvent, shown as the lighter component, enters column 1 at the bottom through line 3 (for a solvent which is heavier, the two feed streams would come in the reversed ends). The purified (or partially purified) I-365 stream is removed from the bottom of column 1 through line 4, and the used, I-141b-enriched, solvent stream is removed from the top of column 1 through line 5. Any solvent adsorbed into the I-365 stream is removed by distillation in column 6, producing a purified I-365 stream which exits the top of column 6 through line 7 and a small solvent recycle stream which exits the bottom of column 6 through line 8 for reintroduction to column 1. The used solvent stream is distilled in distillation column 9 to remove the I-141b (and any I-365) which exits at the top of column 9 through line 10, and then the purified solvent stream is recycled back to column 1 via line 11. A pump 12 provides the power to circulate the solvent around the process.

Figure 2:
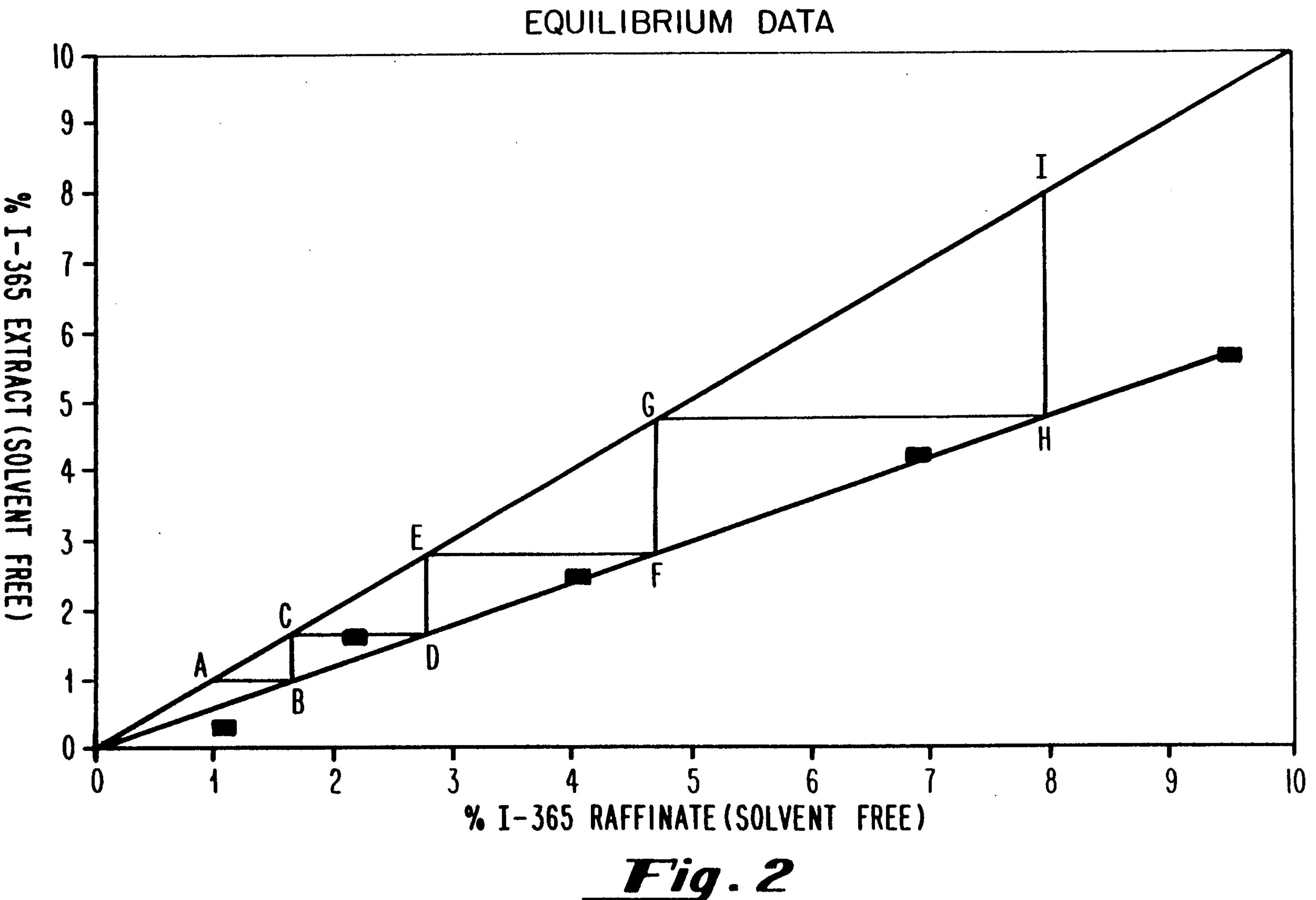
FIG. 2 shows equilibrium data at 25° C. for the ternary system of I-365, I-14lb, and ethylene glycol solvent, and the use of such data for determining equilibrium stages.

The extraction column can be designed from equilibrium data. For example, the Table below shows equilibrium concentrations for the ternary system of I-365, I-141b, and ethylene glycol at 25° C. Plotting of the data as in FIG. 2 enables the design of an on column to reduce I-141b in an I-141b/I-365 stream from, for example, 99% to 92%. Referring to FIG. 2, the I-365 is fed to an extraction column (at point A). The solvent leaves the column (at point B) with 99% I-141b, in equilibrium with I-365 now having an I-141b concentration of only 98.3% (point C). Thus, after leaving the first equilibrium stage of the extraction column (from point A to point C), the I-141b concentration has been reduced from 99% to 98.3%. Using the same procedure (C to E, E to G, and G to I), it is seen that the concentration can be reduced to 92% in four equilibrium stages.

TABLE

Equilibrium Data for I-141b, I-365, and and Solvent at 25° C. (in Mole %)

| I-141b | I-365 (*) | Ethylene Glycol |
|---|---|---|
| | (A) RAFFINATE | |
| 98.9 | 1.1 (1.1) | 0.0 |
| 97.8 | 2.2 (2.2) | 0.0 |
| 96.0 | 4.0 (4.0) | 0.0 |
| 93.1 | 6.9 (6.9) | 0.0 |
| 90.5 | 9.5 (9.5) | |
| | (B) EXTRACT | |
| 7.8 | 0.02 (0.3) | 92.2 |
| 8.2 | 0.13 (1.6) | 91.6 |
| 7.4 | 0.19 (2.4) | 92.4 |
| 6.3 | 0.27 (4.1) | 93.5 |
| 6.1 | 0.36 (5.6) | 93.5 |

*Amounts in Parenthesis Show I-365 On A Solvent-Free Basis

What is claimed is:

1. A method of at least partial separation of a mixture of 1,1,1,3,3-pentafluorobutane and 1,1-dichloro-1-fluoroethane comprising liquid-liquid extraction on said mixture in the presence of an extraction agent containing ethylene glycol, 2-butene-1,4-diol, ethanolamine, propylene glycol, or mixtures thereof.

2. A method of at least partial separation of a mixture of 1,1,1,3,3-pentafluorobutane and 1,1-dichloro-1-fluoroethane comprising liquid-liquid extraction on said mixture in the presence of an extraction agent selected from the group consisting of ethylene glycol alone or in admixture with 2-butene-1,4-diol, ethanolamine, propylene glycol, propylene carbonate, 2-butene-1,4-diol and propylene glycol, 2-butene-1,4-diol and dipropylene glycol, or ethanolamine and dipropylene glycol; 2-butene-1,4-diol alone or in admixture with propylene glycol, ethanolamine, propylene carbonate, ethanolamine and dipropylene glycol, or dipropylene glycol; ethanolamine alone or in admixture with propylene glycol or dipropylene glycol; or propylene glycol.

3. The method of claim 2 wherein the extraction agent is ethylene glycol.

* * * * *